(12) United States Patent
Freeman et al.

(10) Patent No.: US 6,640,130 B1
(45) Date of Patent: Oct. 28, 2003

(54) INTEGRATED IMAGING APPARATUS

(75) Inventors: Jenny E. Freeman, Chestnut Hill, MA (US); Michael J. Hopmeier, Mary Esther, FL (US); M. Leventen, Lexington, MA (US); James Mansfield, Boston, MA (US); Edgar Neil Lewis, Brookeville, MD (US)

(73) Assignee: HyperMed, Inc., Watertown, MA (US)

( * ) Notice: Subject to any disclaimer, the term of this patent is extended or adjusted under 35 U.S.C. 154(b) by 251 days.

(21) Appl. No.: 09/609,544

(22) Filed: Jul. 3, 2000

Related U.S. Application Data
(60) Provisional application No. 60/142,067, filed on Jul. 2, 1999.

(51) Int. Cl.[7] .................................................. A61B 6/00
(52) U.S. Cl. ........................ 600/474; 600/412; 382/128
(58) Field of Search ................................ 600/473, 474, 600/549, 476, 475, 477, 410, 412, 411, 407; 382/128, 130, 131, 234

(56) References Cited

U.S. PATENT DOCUMENTS

| | | | | |
|---|---|---|---|---|
| 5,568,384 A | * | 10/1996 | Robb et al. ................. | 382/132 |
| 5,760,899 A | | 6/1998 | Eismann | |
| 5,782,770 A | | 7/1998 | Mooradian et al. ......... | 600/476 |
| 5,871,013 A | * | 2/1999 | Wainer et al. .............. | 600/407 |
| 6,173,201 B1 | * | 1/2001 | Front ......................... | 600/429 |
| 6,198,957 B1 | * | 3/2001 | Green ........................ | 600/422 |

FOREIGN PATENT DOCUMENTS

| | | | | |
|---|---|---|---|---|
| GB | 2311368 | 9/1997 | ............ | A61B/5/00 |
| WO | WO99/22640 | 5/1999 | ............ | A61B/5/00 |

OTHER PUBLICATIONS

M.G. Sowa, et al., "Assessment of Tissue Viability by Near–IR Spectroscopy and Imaging," *Proc. SPIE*, 3252, 1998, pp. 199–207.

M.G. Sowa, et al., "Near–Infrared Spectroscopic Assessment of Tissue Hydration Following Surgery," *Journal of Surgical Research*, 86, 1999, pp. 62–69.

M.G. Sowa, et al., "Visible–Near Infrared Multispectral Imaging of the Rat Dorsal Skin Flap," *Journal of Biomedical Optics*, 4, 1999, pp. 474–481.

J.R. Mansfield, et al., "The Development of Visible and Near–IR LCTF–based Spectroscopic Imaging Systems for Macroscopic Samples," *International Society of Optical Engineers*, 3920, 2000, pp. 99–107.

R.A. De Blasi, et al., "Oxygen Consumption of Human Skeletal Muscle by Near Infrared Spectroscopy During Tourniquet–Induced Ischemia in Maximal Voluntary Contraction," *Adv. Exp. Med. Biol.*, 317, 1992, pp. 771–777.

M.F. Stranc, et al. "Assessment of Tissue Viability Using Near–Infrared Spectroscopy," *British Journal of Plastic Surgery*, 51, 1998, 21–218.

J.R. Mansfield, et al. "Analysis of Spectroscopic Imaging Data by Fuzzy C–Means Clustering,".

J.R. Mansfield, et al., "Fuzzy C–Means Clustering and Principal Component Analysis of Time Series from Near–Infrared Imaging of Forearm Ischemia," *Computerized Medical Imaging and Graphics*, 21, 1997, pp. 299–308.

(List continued on next page.)

*Primary Examiner*—Philip H. Leung
(74) *Attorney, Agent, or Firm*—Morrison & Foerster LLP

(57) ABSTRACT

The invention is directed to imaging methods for performing real-time or near real-time assessment and monitoring. Embodiments of these methods are useful in a plurality of settings including surgery, clinical procedures, tissue assessment, diagnostic procedures, forensic, health monitoring and medical evaluations.

18 Claims, 1 Drawing Sheet

OTHER PUBLICATIONS

R. Salzer, et al., "Infrared and Raman Imaging of Biological and Biiomimetic Samples," *Fresenius Journal of Analytical Chemistry*, 366, 2000, pp. 712–726.

R.A. Shaw, et al, "Analysis of Biomedical Spectra and Images: From Data to Diagnosis," *Journal of Molecular Structure (Theochem)*, 500, 2000, pp. 129–138.

R.A. Shaw, et al., "In Vivo Optical/Near–Infrared Spectroscopy and Imaging of Metalloproteins," *Journal of Inorganic Biochemistry*, 79, 2000, pp. 285–293.

J.R. Mansfield, et al., "Near Infrared Spectroscopic Reflectance Imaging: Methods for Functional Imaging and In–Vivo Monitoring," *Proc. SPIE Int. Soc. Opt. Eng.*, 3597, 1999, pp. 222–233.

J.R. Mansfield, et al., "LDA–Guided Search Engine for the Nonsubjective Analysis of Infrared Microscopic Maps," *Applied Spectroscopy*, 53, 1999, pp. 1323–1330.

L. M. McIntosh, et al., "Analysis and Interpretation of Infrared Microscopic Maps: Visualization and Classification of Skin Components by Digital Staining and Multivariate Analysis," *Biospectroscopy*, 5, 1999, pp. 265–275.

J.R. Mansfield, et al., "Near Infrared Spectroscopic Reflectance Imagining: Supervised Vs. Unsupervised Analysis Using an Art Conservation Application," *Vibrational Spectroscopy*, 19, 1999, pp. 33–45.

J.R. Payette, et al., "Noninvasive Diagnostics: Predicting Flap Viability with Near–IR Spectroscopy and Imaging," *American Clinical Laboratory*, 18, 1999, pp. 4–6.

J.R. Mansfield, et al., "Tissue Viability by Multispectral Near Infrared Imaging: A Fuzzy C–Means Clustering Analysis," *IEEE Transactions on Medical Imaging*, 6, 1998, pp. 1011–1018.

M.G. Sowa, et al., "Noninvasive Assessment of Regional and Temporal Variations in Tissue Oxygenation by Near–Infrared Spectroscopy and Imaging," *Applied Spectroscopy*, 51, 1997, pp. 143–152.

M. E. Leventon, "Statistical Modes in Medical Image Analysis," *MIT Ph.D. Thesis*, May 2000.

B.K.P. Horn, "Closed–Form Solution of Absolute Orientation Using Unit Quaternions," *Journal of the Optical Society of America*, 4, 1987, pp. 629–642.

V.R. Mandava, et al., "Registration of Multimodal Volume Head Images Via Attached Markers," *Proc SPIE*, 1652, 1992, pp. 271–282.

J. West, et al., "Comparison and Evaluation of Retrospective Intermodality Image Registration Techniques," *Proc SPIE*, 2710, 1996, pp. 332–347.

J.B. A. Maintz, "Comparison of Feature–Based Matching of CT and MR Brain Images," *Computer Vision, Virtual Reality and Robotics in Medicine*, 1995, pp. 212–228.

G.Q. Maguire, Jr., et al., "Graphics Applied to Medical Image Registration," *IEEE Computer Graphics Appications*, 11, 1991, pp. 20–29.

S. Xuegang, et al., "Developing System for the Real–Time Fusing of Infrared and Visible Light Images," *International Symposium on Multispectral Image Processing, Proceedings of the SPIE–The International Society for Optical Engineering, USA*, vol. 3545, Oct. 21–23, 1998, pp. 574–577.

H. Jiang, et al., "A New Approach to 3–D Registration of Multimodality Medical Images by Surface Matching," *Proc. SPIE*, 1808, 1994, pp. 45–56.

D. Lemoine, et al., "Multimodal Registration System for the Fusion of MRI, CT, MED and 3D or Stereotactic Angiographic Data," *Proc. SPIE*, 2164, 1994, pp. 45–56.

C.A. Pelizzari, et al., "Accurate Three–Dimensional Registration of CT, PET, and/or MR Images of the Brain," *J Comput Assist. Tomogr.*, 13, 1989, pp. 20–26.

G.J. Ettinger, "Hierarchical Three–Dimensional Medical Image Registration," *MIT PhD. Thesis*, Jun. 1997.

P.A. van den Elsen, et al., "Grey Value Correlation Techniques Used for Automatic Matching of CT and MR Brain and Spine Images," *Proc SPIE*, 2359, 1994, pp 227–237.

A. J. Bell, et al., "A Non–Linear Information Maximisation Algorithm that Performs Blind Separation," *Advances in Neural Information Processing*, 7, 1995, pp. 467–474.

A. Collignon, et al., "3D Multi–Modality Medical Image Registration Using Feature Space Clustering," *First Conf. on Computer Vision, Virtual Reality and Robotics in Medicine Springer*, pp. 195–204.

F. Maes, et al., "Multimodality Image Registration by Maximization of Mutual Information," *IEEE Transactions on Medical Imaging*, vol. 16, No. 2, Apr. 1997, pp. 187–198.

W.M. Wells, et al., "Multi–modal Volume Registration by Maximization of Mutual Information," *Medical Image Analysis*, vol. 1, No. 1, 1996, pp. 35–51.

M. Leventon, et al., "Three–Dimensional Reconstruction and Surgical Navigation in Pediatric Epilepsy Surgery," *MIT Report*, Massachusetts Institute of Technology, Cambridge, MA, Dec. 1998.

A. Chabreie, et al., "Three–Dimensional Reconstruction and Surgical Navigation in Pediatric Epilepsy Surgery," *Proceedings First International Conference on Medical Image Computing and Computer–Assisted Interventions MICCAI'98*, Massachusetts Institute of Technology, Cambridge, MA, Oct. 11–13, 1998.

Quarantelli et al. "Frequency encoding for simultaneous display of multimodality images" Journal of Nuclear Medicine, vol. 40, No. 3, Mar. 1999, pp. 442–447.

Williams et al "A Novel Method for Non–Invasive Multispectral Imaging of Tissue" Proceedings of IEEE Southeastcon 1992, vol. 1, Apr. 1992, pp. 291–294.

* cited by examiner

INTEGRATED IMAGING APPARATUS

REFERENCE TO RELATED APPLICATIONS

This application claims priority to U.S. Provisional Patent Application, Ser. No. 60/142,067, filed Jul. 2, 1999.

BACKGROUND OF THE INVENTION

1. Field of the Invention

The invention is directed to an imaging apparatus and methods for performing assessment and monitoring with interpreted imaging. Embodiments of the invention are particularly useful in surgery, clinical procedures, tissue assessment, diagnostic procedures, health monitoring, and medical evaluations.

2. Description of the Background

Spectroscopy, whether it is visible, near infrared, infrared or Raman, is an enormously powerful tool for the analysis of biomedical samples. The medical community, however, has a definite preference for imaging methods, as exemplified by methods such as MRI and CT scanning as well as standard X-ray photography and ultrasound imaging. This is entirely understandable as many factors need to be taken into account for a physician to make a clinical diagnosis. Imaging methods potentially can provide far more information to a physician than their non-imaging counterparts. With this medical reality in mind, there has been considerable effort put into combining the power and versatility of imaging method with the specificity of spectroscopic methods.

Near-infrared (near-IR) spectroscopy and spectroscopic imaging can measure the balance between oxygen delivery and tissue oxygen utilization by monitoring the hemoglobin oxygen saturation in tissues (Sowa, M. G. et al., 1998, *Proc. SPIE* 3252, pp. 199–207; Sowa, G. W. et al., 1999, *Journal of Surgical Research*, 86:62-29; Sow, G. W. et al., 1999, *Journal of Biomedical Optics*, 4:474–481; Mansfield, J. R., et al., 2000, *International Society of Optical Engineers*, 3920:99–197). For in-vivo human studies, the forearm or leg has been the investigational site for many of the noninvasive near-IR studies. Non-imaging near-IR applications have examined the local response of tissue to manipulations of blood flow (De-Blasi, R. A. et al., 1992, *Adv. Exp. Med. Biol*, 317:771–777). Clinically, there are situations where the regional variations in oxygenation saturation are of interest (Stranc, M. F. et al, 1998, *British Journal of Plastic Surgery*, 51:210–218). Near-IR imaging offers a means of accessing the spatial heterogeneity of the hemoglobin oxygenation saturation response to tissue perfusion. (Mansfield, J. R. et al., 1997, *Analytical Chemistry*, 69:3370–3374; Mansfield, J. R., et al., 1997, *Computerized Medical Imaging and Graphics*, 21:299–308; Salzer, R., et al., 2000, *Fresenius Journal of Analytical Chemistry*, 366:712–726; Shaw, R. A., et al., 2000, *Journal of Molecular Structure (Theochem)*, 500:129–138; Shaw, R. A., et al., 2000, *Journal of Inorganic Biochemistry*, 79:285–293; Mansfield, J. R., et al., 1999, *Proc. SPIE Int. Soc. Opt. Eng.*, 3597:222–233; Mansfield, J. R., et al., 1999, *Applied Spectroscopy*, 53:1323–1330; McIntosh, L. M., et al., 1999, *Biospectroscopy*, 5:265–275; Mansfield, R., et al., *Vibrational Spectroscopy*, 19:33–45; Payette, J. R., et al., 1999, *American Clinical Laboratory*, 18:4–6; Mansfield, J. R., et al., 1998, *IEEE Transactions on Medical Imaging*, 6:1011–1018

Non-invasive monitoring of hemoglobin oxygenation exploits the differential absorption of $HbO_2$ and Hb, along with the fact that near-IR radiation can penetrate relatively deeply into tissues. Pulse oximetry routinely supplies a noninvasive measure of arterial hemoglobin oxygenation based on the differential red-visible and near infrared absorption of Hb and $HbO_2$. Visible/near-IR multispectral imaging permits the regional variations in tissue perfusion to be mapped on macro and micro scale. Unlike infrared thermography, hyperspectral imaging alone does not map the thermal emission of the tissues. Instead, this imaging method relies on the differential absorption of light by a chromophore, such as, Hb and $HbO_2$, resulting in differences in the wavelength dependence of the tissue reflectance depending on the hemoglobin oxygen saturation of the tissue. (Sowa, M. G., et al., 1997, *Applied Spectroscopy*, 51:143–152; Leventon, M., 2000, MIT Ph.D. Thesis)

Spectroscopic imaging methodologies and data are becoming increasingly common in analytical laboratories, whether it be magnetic resonance (MRI), mid-IR, Raman, fluorescence and optical microscopy, or near-IR/visible-based imaging. However, the volume of information contained in spectroscopic images can make standard data processing techniques cumbersome. Furthermore, there are few techniques that can demarcate which regions of a spectroscopic image contain similar spectra without a priori knowledge of either the spectral data or the sample's composition. The objective of analyzing spectroscopic images is not only to determine what the spectrum is at any particular pixel in the sample, but also to determine which regions of the sample contain similar spectra; i.e., what regions of the sample contain chemically related compounds. Multivariate analysis methodologies can be used to determine both the spectral and spatial characteristics of a sample within a spectroscopic imaging data set. These techniques can also be used to analyze variations in the temporal shape of a time series of images either derived for extracted from a time series of spectroscopic images.

There are few techniques that can demarcate which regions of a sample contain similar substances without a priori knowledge of the sample's composition. Spectroscopic imaging provides the specificity of spectroscopy while at the same time relaying spatial information by providing images of the sample that convey some chemical meaning. Usually the objective in analyzing heterogeneous systems is to identify not only the components present in the system, but their spatial distribution. The true power of this technique relative to traditional imaging methods lies in its inherent multivariate nature. Spatial relationships among many parameters can be assessed simultaneously. Thus, the chemical heterogeneity or regional similarity within a sample is captured in a high dimensional representation which can be projected onto a number of meaningful low dimensional easily interpretable representations which typically comprise a set of composite images each having a specific meaning.

While it is now clear that both spectroscopy and spectroscopic imaging can play roles in providing medically relevant information, the raw spectral or imaging measurement seldom reveals directly the property of clinical interest. For example using spectroscopy, one cannot easily determine whether the tissue is cancerous, or determine blood glucose concentrations and the adequacy of tissue perfusion. Instead, pattern recognition algorithms, clustering methods, regression and other theoretical methods provide the means to distill diagnostic information from the original analytical measurements.

There are however various methods for the collection of spectroscopic images. In all such cases, the result of a spectroscopic imaging experiment is something termed a spectral image cube, spectroscopic imaging data cube or just hypercube. This is a three dimensional array of data, consisting of two spatial dimensions (the imaging component), and one spectral dimension. It can be thought of as an array of spatially resolved individual spectra, with every pixel in the first image consisting of an entire spectrum, or as a series of spectrally resolved images. In either representation, the 3D data cube can be treated as a single entity containing enormous amounts of spatial and spectral information about the sample from which it was acquired.

As an extension of the three dimensional array acquired in a spectroscopic imaging experiment, one can collect data cubes as a function of additional parameters such as time, temperature or pH. Numerous algorithms can be used to analyze these multi-dimensional data sets so that chemical and spectral variations can be studied as additional parameters. However, taken together, they can allow one to more fully understand the variations in the data. This can be done in a gated or sequential fashion.

Multi-modal image fusion, or image registration, is an important problem frequently addressed in medical image analysis. Registration is the process of aligning data that arise from different sources into one consistent coordinate frame. For example, various tissues appear more clearly in different types of imaging methods. Soft tissue, for example, is imaged well in MR scans, while bone is more easily discernible in CT scans. Blood vessels are often highlighted better in an MR angiogram than in a standard MR scan. Multiple scans of the same patient will generally be unregistered when acquired, as the patient may be in different positions in each scanner, and each scanner has its own coordinate system. In order to fuse the information from all scans into one coherent frame, the scans must be registered. The very reason why multiple scans are useful is what makes the registration process difficult. As each modality images tissue differently and has its own artifacts and noise characteristics, accurately modeling the intensity relationship between the scans, and subsequently aligning them, is difficult.

The registration of two images consists of finding the transformation that best maps one image into the other. If $I_1$ and $I_2$ are two images of the same tissue and T is the correct transformation, then the voxel $I_1(x)$ corresponds to the same position in the sample as the voxel $I_2(T(x))$. In the simplest case, T is a rigid transformation consisting of three degrees of freedom of rotation and three degrees of freedom of translation. The need for rigid registration arises primarily from the patient being in different positions in the scanning devices used to image the anatomy. The information from all the images is best used when presented in one unified coordinate system. Without such image fusion, the clinician must mentally relate the information from the disparate coordinate frames.

One method of aligning the two images is to define an intermediate, patient-centered coordinate system, instead of trying to directly register the images to one another. An example of a patient-centered reference frame is the use of fiducial markers attached to a patient throughout the various image acquisitions. The fiducial markers define a coordinate system specific to the patient, independent of the scanner or choice of imaging modality. If the markers remain fixed and can be accurately localized in all the images, then the volumes can be registered by computing the best alignment of the corresponding fiducials (Horn, B. K. P., 1987, *Journal of the Optical Society of America A*, 4:629–642; Mandava, V. R., et al., *Proc SPIE*, 1992, 1652:271–282; Haralick, R. M., et al., 1993, *Computer and Robot Vision*). The main drawback of this method is that the markers must remain attached to the patient at the same positions throughout all image acquisitions. For applications such as change detection over months or years, this registration method is not suitable. Fiducial registration is typically used as groundtruth to evaluate the accuracy of other methods as careful placement and localization of the markers can provide very accurate alignment (West, J. et al., 1996, *Proc SPIE*, Newport Beach, Calif.).

When fiducial markers are not available to define the patient coordinate frame, corresponding anatomical feature points can be extracted from the images and used to compute the best alignment (Maintz, J. B. Antione, et al., 1995 *Computer Vision, Virtual Reality and Robotics in Medicine*, pp. 219–228; Maguire, Jr., G., et al., 1991, *IEEE Computer Graphics Applications*, 11:20–29). This approach depends greatly on the ability to automatically and accurately extract reliable image features. In general, methods of feature extraction such as intensity thresholding or edge detection do not work well on medical scans, due to non-linear gain fields and highly textured structures. Even manual identification of corresponding 3D anatomical points can be uireliable. Without the ability to accurately localize corresponding features in the images, alignment in this manner is difficult.

Instead of localizing feature points in the images, richer structures such as object surfaces can be extracted and used as a basis of registration. A common method of registering MR and CT of the head involves extracting the skin (or skull) surfaces from both images, and aligning the 3D head models (Jiang, H., et al., 1992 *Proc. SPIE*, 1808:196–213; Lemoine, D. et al., 1994, *Proc. SPIE*, 2164:46–56). For PET/MR registration, the brain surface is typically used since the skull is not clearly visible in PET (Pelizzari, C., et al., *J Comput Assist. Tomogr.*, 1989, 13:20–26). The 3D models are then rigidly registered using surface-based registration techniques (Ettinger, G., 1997, MIT Ph.D Thesis). The success of such methods relies on the structures being accurately and consistently segmented across modalities and the surfaces having rich enough structure to be unambiguously registered.

Voxel-based approaches to registration do not extract any features from the images, but use the intensities themselves to register the two images. Such approaches model the relationships between intensities of the two images when they are registered, and then search through the transformation space to find an alignment that best agrees with the model. Various intensity models are discussed, including correlation, mutual information, and joint intensity priors.

Correlation is a measure commonly used to compare two images or regions of images for computer vision problems such as alignment or matching. Given the intensity values of two image patches stacked in the vectors u and v, the normalized correlation measure is the dot product of unit vectors in the directions of u and v:

$$(u \cdot v)/(\|u\|\|v\|)$$

An advantage of correlation-based methods is that they can be computed quite efficiently using convolution operators. Correlation is applicable when one expects a linear relationship between the intensities in the two images. In computer vision problems, normalized correlation provides some amount of robustness to lighting variation over a measure such as sum of square differences (SSD), $\|u-v\|^2$. The primary reason for acquiring more than one medical scan of a patient stems from the fact that each scan provides different information to the clinician. Therefore, two images that have a simple linear intensity relationship may be straightforward to register, but do not provide any additional information than one scan by itself. On the other hand, if the images are completely independent (e.g. no intensity relationship exists between them), then they cannot be registered using voxel-based methods. In general, there is some dependence between images of different modalities and each modality does provide additional information.

One simplified model of the medical imaging process is that an internal image is a rendering function R of underlying tissue properties, P(x), over positions x. An image of modality A could be represented as a function $R_A(P)$ and a registered image of modality B of the same patient would be another function, say $R_B(P)$. Suppose a function F(x) could be computed relating the two rendering functions such that the following is true (with the possible addition of some Gaussian noise, N):

$$F(R_B(P))=R_A(P)+N$$

The function F would predict the intensity at a point in Image A given the intensity at the corresponding point in Image B. Such a function could be used to align a pair of images that are initially in different coordinate systems using SSD:

$$T^*=\mathrm{argmin}_T\Sigma_x(F(R_B(P(X)))-R_A(P(x)))^2$$

where T is the transformation between the two sets of image coordinates. Van den Elsen et al. compute such a mapping that makes a CT image appear more like an MR, and then register the images using correlation (van den Elsen, P., et al., 1994, "Visualization in Biomedical Computing," 1994 Proc SPIE, 2359:227–237). In general, explicitly computing the function F that relates two imaging modalities is difficult and under-constrained.

Maximization of mutual information (MI) is a general approach applicable to a wide range of multi-modality registration applications (Bell, A. J., et al., 1995 Advances in Neural Information Processing 7; Collignon, D., et al., 1995, First Conf. on Computer Vision, Virtual Reality and Robotics in Medicine Springer; Maes, F. et al, 1996, Mathematical Methods in Biomedical Image Analysis; Wells, W. M., et al., 1996, Medical Image Analysis, 1(1):35–51). One of the strengths of using mutual information is that MI does not use any prior information about the relationship between joint intensity distributions. While mutual information does not explicitly model the function F that relates the two imaging modalities, it assumes that when the images are aligned, each image should explain the other better than when the images are not aligned.

Given two random variables U and V, mutual information is defined as (Bell, 1995):

$$MI(U,V)=H(U)+H(V)-H(U,V)$$

where H(U) and H(V) are the entropies of the two variables, and H(U,V) is the joint entropy. The entropy of a discrete random variable is defined as:

$$H(U)=-\Sigma P_u(u) \log P_u(u)$$

where $P_u(u)$ is the probability mass function associated with U. Similarly, the expression for joint entropy entropy operates over the joint PDF:

$$H(U,V)=-\Sigma\Sigma P_{u,v}(u,v) \log P_{u,v}(u,v)$$

When U and V are independent, H(U,V)=H(U)+H(V), which implies the mutual information is zero. When there is a one-to-one functional relationship between U and V, (i.e. they are completely dependent), the mutual information is maximized as:

$$MI(U,V)=H(U)=H(V)=H(U,V)$$

To operate on images over a transformation, we consider the two images, $I_1(x)$ and $I_2(x)$ to be random variables under a spatial parameterization, x. We seek to find the value of the transformation T that maximizes the mutual information (Wells, 1996):

$$T^*=\mathrm{argmax}_T MI(I_1(x),I_2(T(x)))$$

$$T^*=\mathrm{argmax}_T H(I_1(x))+H(I_2(T(x)))-H(I_1(x),I_2(T(x)))$$

The entropies of the two images encourage transformations that project I1 onto complex parts of I2. The third term, the (negative) joint entropy of $I_1$ and $I_2$, takes on large values when X explains Y well. Derivatives of the entropies with respect to the pose parameters can be calculated and used to perform stochastic gradient ascent (Wells, 1996). West et al. compare many multi-modal registration techniques and find mutual information to be one of the most accurate across all pairs of modalities (West, 1996).

Leventon et al. introduced an approach to multi-modal registration using statistical models derived from a training set of images (Leventon, M., et al., 1998, *Medical Image Computing and Computer-assisted Intervention*). The method involved building a prior model of the intensity relationship between the two scans being registered. The method requires a pair of registered training images of the same modalities as those to be registered in order to build the joint intensity model. To align a novel pair of images, the likelihood of the two images given a certain pose based on our model by sampling the intensities at corresponding points is computed. This current hypothesis can be improved by ascending the log likelihood function. In essence, one computes a probabilistic estimate of the function F (that relates the two imaging modalities) based on intensity co-occurrence. To align the novel images, the pose is found that maximizes the likelihood that those images arose from the same relation F.

Building a joint-intensity model does require having access to a registered pair of images of the same modality and approximately the same coverage as the novel pair to be registered. Mutual information approaches do not need to draw upon previously registered scans. However, when this information is available, the prior joint intensity model provides the registration algorithm with additional guidance which results in convergence on the correct alignment more quickly, more reliably and from more remote initial starting points.

SUMMARY OF THE INVENTION

The present invention overcomes problems and disadvantages associated with current strategies and designs and provides methods and apparatus for imaging using real-time or near real-time assessment and monitoring. Embodiments of the device are useful in a plurality of settings including surgery, clinical procedures, tissue assessment, diagnostic procedures, forensic, health monitoring and medical evaluations.

One embodiment of the invention is directed to an imaging apparatus comprising integrating spatial, spectral and temporal features, and optionally other physiologic or relevant data, such as room temperature or ambient light, in a spectral and temporal multimodal imaging system for the evaluation of biological systems and stimuli and fusing one or more thermal images or other imaging modalities and hyperspectral data cube for assessment of biological processes. The integrated features may comprise two or more of visible or infrared hyperspectral images, visible or infrared brightfield images, thermal images, fluorescence images, Raman images and/or other relevant imaging modalities. The imaging apparatus may further comprise a specific UV, visible and/or infrared light source, and means for collecting two or more of visible or infrared hyperspectral images, visible or infrared brightfield images, thermal images, fluorescence images, Raman images, or standard video images.

Another embodiment of the invention is directed to methods for detecting a diseased condition comprising acquiring thermal images from a target, acquiring visible or infrared hyperspectral images from the same target, fusing the thermal images and visible or infrared hyperspectral images to analyze spatial distributions and/or feature determination of the target. Thermal images or hyperspectral images of the target and/or other data can be interlaced with a time dependent reference to determine changes which could influence and be correlated with results from other imaging modalities. Wavelengths can be selected to maximize diagnostic information for a specific tissue state or anticipated end diagnostic goal. The selection step involves performing multivariate image and spectral processing using multivariate image and spectral processing algorithms to extract information from the plurality of images and spectra for real-time or near real-time assessment. Multiple hyperspectral collection devices in a variety of wavelength regimens could be used simultaneously or sequentially or on an as needed basis. For instance a visible hyperspectral images could be combined with a near infrared hyperspectral imager (plus or minus a broad band thermal camera) to provide combined information from both wavelength regions. In this way, one can analyze tissue health mapping; skin sebum level mapping; skin dryness, skin texture, skin feel or skin color mapping; skin damage detection and mapping (UV damage, frostbite, bums, cuts, abrasions) impact of cosmetics or other substances applied to the skin bruise age, force of impact, peripheral vascular disease diagnosis, extent, determination or regionalization of ischemia, varicose veins or hemorrhage detection, local detection and mapping, systemic infection detection, differentiation between viral, bacterial and fungal, and more specific identification, such as between gram negative and gram positive bacterial infection, venous occlusion increase in total hemoglobin, hematocrit, and change in deoxyhemoglobin/oxyhemoglobin ratio, differentiate between ischemia and hypoxia, bum depth and wound healing evaluation, non-invasive diagnosis of shock by imaging uninjured skin, hemorrhagic shock, septic shock, bum shock, changes in a dynamic system as a function of time or other parameter, vascular occlusion, vaso-dilation and vaso-constriction changes related to the presence of cancer in primary tissue or lymph nodes, either surface or subsurface, changes related to a specific chemical, mechanical, thermal, pharmacological or physiological stimulus. Different levels of microvascular constriction and relaxation lead to different ratios of oxyhemoglobinldeoxyhemoglobin, to tissue perfusion, tissue abnormality, disease state or diagnostic condition, total hematocrit, differentiate differences in reperfusion state following occlusion where oxygenation levels may remain low although there is good perfusion.

Other technical advantages of the present invention are set forth in or will be apparent from drawings and the description of the invention which follows, or may be learned from the practice of the invention.

DESCRIPTION OF THE INVENTION

Figure 1:
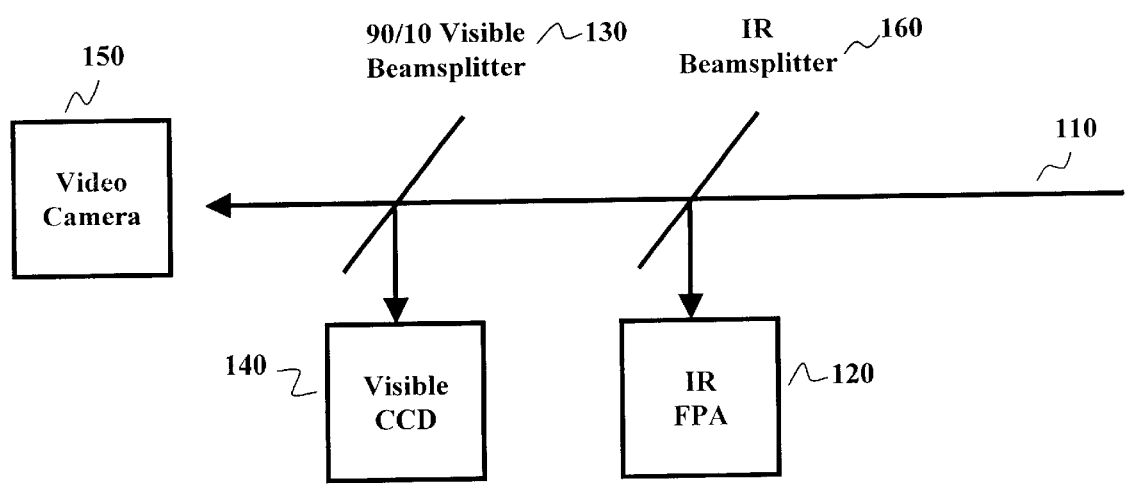
FIG. 1 A schematic diagram of a common optical path shared by multiple modalities.

As embodied and broadly described herein, the present invention is directed to an imaging apparatus and methods for performing real-time or near real-time assessment and monitoring. Embodiments of the device are useful in a plurality of settings including surgery, clinical procedures, tissue assessment, diagnostic procedures, forensic, health monitoring and medical evaluations.

It has been surprisingly found that the pairing of hyperspectral imaging data with data obtained from other single-image imaging methodologies, (examples of which include thermal imaging or fluorescence imaging) provides a sensitive and accurate assessment measure of a physiological condition. This is particularly appealing in terms of tissue assessment in that both thermal perfusion assessments and various multi-modal tissue signatures which incorporate things such as oxyhemoglobin/deoxyhemoglobin ratios and other indices of tissue physiology, pathology or function are interrelated. By fusing data from multiple collection devices and multiple spectral modalities, such as a broad band thermal camera and one or more hyperspectral cameras, or a single imaging device that can respond in multiple discreet bands, data can be obtained to provide medically relevant information. Additionally, pixel to pixel registration for fusion will benefit from methodologies designed to permit this. Included among these technologies are Automatic Target Recognition (ATR), a technology developed within the military for automatic analysis and pattern recognition of signature data, and gating of images relative to repetitive physiological parameters such as heart rate or respiration. In an embodiment of the invention, an ATR is used to maintain image centering. The addition of such novel features as a common optical path optimizes data collection and minimizes processing requirements for a fused image. Image fusion between hyperspectral image datasets (also referred to as cubes) and other imaging modalities would allow for the extraction of more medically-relevant features and diagnostic information than any of the modalities alone. Addition of physiologically or medically related scalar variables to the data set of one or more hyperspectral imaging sets with or without formal image fusion being required allows for the enhancement of diagnostic algorithms.

Incorporation of a stable broad band light source with the ability to be filtered to provide illumination, either singly or in multiples of different spectral regions, an electronically tunable imaging spectrometer, a video camera, a CCD, and a parfocal infrared focal plane array or other camera with the same field of view as the CCD.

Image fusion using beam splitters for the simultaneous acquisition of multiple discreet images incorporating spectral data, each discreet image providing a unique information set, and these various information sets are combined in a variety of manners to allow for enhanced and more unique signatures. Enhancement results in a broader and more discernible identification methodology. If desired, data analysis can be enhanced by triangulation with two cameras. Polarizing imagers may be used as desired to enhance signatures for various targets. Temporal analysis is included in a signature. Temporal alterations or heterogeneity, with or without a meaningful pattern, is acquired with or without gating.

Thermal images or hyperspectral images, either singly or in combination with other modal images, may be used as an interlaced, time dependent reference to identify changes in the dynamic system. These changes may influence and be correlated with the results from all modalities.

Referring to FIG. 1, signal beam 110 is acquired and IR Beam-splitter 160 is placed in the path of signal beam 110 and accordingly, splits or diverts a portion of the infra-red signal beam 110 to infra-red focal plane array 120. 90/10 Visible Beam-splitter 130 is placed in signal beam 110 behind IR Beamsplitter 160. Visible Beam-splitter 130 splits the visible spectrum of signal beam 110 into two portions, wherein one portion is received by video camera 150, and the other is received by visible camera 150. One or multiple mirrors can be used for the beam splitter. This allows for the simultaneous acquisition of data from multiple modalities.

Fusion of broad band infrared and hyperspectral imaging methodologies may be useful to devise algorithms for wavelength selection that maximize the diagnostic information for a specific tissue state; employ various multivariate image processing algorithms to extract information from the hyperspectral images and spectra and the thermal images for real-time or near real-time assessment of tissue state; devise image processing algorithms to assess the size and shape of abnormal tissue regions or domains; acquire sequential hyperspectral imaging cubes, thermal images or other physiological data to examine changes in a dynamic system as a function of time. Utility is extended by pairing more superficial data from hyperspectral imaging cubes with deeper perfusion data.

According to an embodiment of the present invention, a method for determining a total hematocrit comprises measuring a spatial distribution of oxyhemoglobin, deoxyhemoglobin and methemoglobin using hyperspectral imaging methods within the visible range or infrared range of the electromagnetic spectrum; determining total hematocrit by calculating the area under the oxyhemoglobin, deoxyhemoglobin and methemoglobin spectrum or the intensity at their respective wavelengths; and pairing this with perfusion data from broad band thermal camera to permit assessment of total blood volume.

Alternatively, the invention may be used to determine blood flow within a patient. For example, a thermal camera demonstrates a state of perfusion and a hyperspectral camera demonstrates a state of oxygen extraction. Spatial characteristics relative to blood vessel assist diagnosis, i.e., like mottling visible in skin, and can see more or less heterogeneity under certain thermal, neurohumoral, physiological or pathological circumstances and in specific spatial patterns. In addition, the present invention may be used to determine a static or dynamic response of tissue or musculature when applying an active stimulus, such as a thermal change, drug injection, and electromagnetic or mechanical stimulus.

Different levels of microvascular constriction lead to different ratios of blood oxy/deoxygenation or signature of tissue vs. artery vs. vein. In addition to heme and heme-containing or related components, many chemicals and substances can be identified including, for example, glucose, enzymes and metabolic effluents, and moisture content and distribution can be determined and calibrated with artery verses vein. Arterial occlusion causes a decrease in perfusion and total hemoglobin and increase in deoxyhemoglobin/oxyhemoglobin ratio. The time course will be useful as well as including both first and second derivatives. Arterial reperfusion causes increase in perfusion and total hemoglobin. This increase in perfusion, leads to decreased differences between artery and tissue and vein for both hemoglobin saturation and thermal differences. This is due to a decreased resistance to flow at the arteriolar level. Venous occlusion causes an increase in total hemoglobin, hematocrit, and an increase in deoxyhemoglobin/oxyhemoglobin ratio. The time course also varies with arterial occlusion and oxyhemoglobin/deoxyhemoglobin ratios.

Artery and vein measurements can be used as internal calibration on a given picture for tissue levels of oxyhemoglobin/deoxyhemoglobin or thermal image or signature. Further, one can add thermal data by fusing thermal image just as one of the wavelengths in series in hyperspectral cube, i.e., an extra plane. Alternatively, thermal images can be fused to each wavelength image in series. Alternatively or in addition, generic processed analysis of thermal image (degree of variation) weights an image of each wavelength plane or impacts hyperspectral algorithmic analysis. Scalar data presenting physiologic or other relevant data can be also incorporated as described above.

According to an embodiment of the present invention, correction for a patient's motion is done by tissue stabilization or in the case of repetitive motions by gating image frames with a patient's cardiac or respiration cycle. Frames at the specific wavelengths selected for a particular diagnostic module are acquired at the same position in sequential cardiac cycles. The timing of the cardiac cycle is provided by electrocardiogram or cardiac ultrasound or other method. The respiratory variation is timed with an external sensor of respiration or with either the ventilating mechanism or a sensor mechanism of an artificial respirator.

The present invention may be used to provide signatures of tissue viability or cancer. Markers of cell viability include hyperspectral signatures of oxyhemoglobin and deoxyhemoglobin or other chromaphores, thermal signatures, or fused signatures. The present invention is used to determine drug impact on vasodilitation, neurohumoral response, physiology, and pathology. The present invention is used to identify and classify a large variety of chemical species, for example, those other than oxyhemoglobin and deoxyhemoglobin. Sensor/image fusion permits additional data acquisition and incorporation into diagnostic assessment. This is facilitated by the use of multiple optical paths properly aligned to optimize registration. Inclusion of simultaneous recording of standard video camera images facilitates registration and provides additional data. False color imaging may be added real-time to facilitate the rapid understanding of the data presented to the surgeon or other user. On board CCD chip filters can be provided to increase processing speed. Input for physiologic monitoring systems, such as blood pressure, heart rate, peripheral oxygenation, can be added to the data acquired and fed into diagnostic algorithms. A recording system can be included to log the real-time or near real-time output of imaging systems.

In an embodiment of the present invention, a split frame video display is used to show all modes simultaneously. For example, parameters of wound healing may be displayed, such as: oxyhemoglobin or deoxyhemoglobin independently or as a ratio; signatures associated with rapidly dividing cells or dead cells, or particular types of cells; fluid content; hydration/dehydration or edema of tissue; or tissue performance. Tissue perfusion data provided by a thermal camera increases accuracy, delivers information about underlying vascular, beds, and/or provides data that will minimize the hyperspectral data processing requirements. Thermal images are used provide a baseline to track oxygen extraction or signature changes induced by tissue exposure.

Increased heterogeneity and spatial features can be important in a diagnosis. For example, in vasoconstriction, it allows identification of areas that are less well perfused small micro areas that manifest as heterogeneity, to be diagnosed. Differences in oxyhemoglobin and deoxyhemoglobin ratios with spatial characteristics provide an image of micromottling. If vasodilated are more uniform, the patterns of vasoconstriction are helpful in diagnosis of infection in general and can aid in the identification of specific infection. Other patterns of heterogeneity are seen with cancers, and for example are associated with areas of increased metabolism or necrosis.

The present invention may be used to analyze tissue health mapping; skin sebum level mapping; skin dryness, skin texture, skin feel or skin color mapping; skin damage detection and mapping (UV damage, frostbite, bums, cuts, abrasions) impact of cosmetics or other substances applied to the skin bruise age, force of impact, peripheral vascular disease diagnosis, extent, determination or regionalization of ischemia, varicose veins or hemorrhage detection, local detection and mapping, systemic infection detection, differentiation between viral, bacterial and fungal, and more specific identification, such as between gram negative and gram positive bacterial infection, venous occlusion increase in total hemoglobin, hematocrit, and change in deoxyhemoglobin/oxyhemoglobin ratio, differentiate between ischemia and hypoxia, bum depth and wound healing evaluation, non-invasive diagnosis of shock by imaging uninjured skin, hemorrhagic shock, septic shock, burn shock, changes in a dynamic system as a function of time or other parameter, vascular occlusion, vaso-dilation and vaso-constriction changes related to the presence of cancer in primary tissue or lymph nodes, either surface or subsurface, changes related to a specific chemical, mechanical, thermal, pharmacological or physiological stimulus. Different levels of microvascular constriction and relaxation lead to different ratios of oxyhemoglobin/deoxyhemoglobin, to tissue perfusion, tissue abnormality, disease state or diagnostic condition, total hematocrit, differentiate differences in reperfusion state following occlusion where oxygenation levels may remain low although there is good perfusion.

In an embodiment of the present invention, motion artifacts of the measurements are used to measure heterogeneity. With motion, a homogeneous tissue will continue to produce the same spectral signature, whereas heterogeneous tissue will demonstrate a variety of different signatures. Extraneous motion artifacts can be reduced by mechanical stabilization of field of regard, for example, by clamping tissue or region of interest. Even in the absence of discrete spatial information, the simple range of spectra obtained, demonstrating the heterogeneity per se can be useful. Dilation makes thermal imaging more uniform and constriction more heterogeneous. The latter correlates with ischemia, microvascular mottling or the edge of larger vessels. Different changes would be detected in association with tumors, immunologic response to infection or other stimulus. Spatial patterns will vary with pathological or physiological differences. Motion artifacts are used as an indicator of inhomogeneous distributions of oxygenation and perfusion. Increases or decreases in artifacts not related to motion are used to assess heterogeneity of oxygenation and perfusion, and, hence, viability.

The present invention may be used to look for signs of perfusion vs. viability. Integration of spatial and spectral and temporal features allows for the diagnosis of viability by creating a perfusion viability matrix. Because blood flow has a temporal component, the amount of blood that gets to tissue may be measured. This can be useful in the assessment of viability, cancer or infection.

In an embodiment of the present invention, images are correlated with pain and drug response to provide pain feedback with infusion; other drug levels, to provide positive/negative feedback. Surface heterogeneity is correlated with infection, to provide determine time of infection, severity, systemic vs. local infection, type of organism, bacterial vs. viral, gram positive versus gram negative The present invention is also used to detect drug usage.

The present invention may also be used for the assessment of metabolism and nutrition. Tissue structure and function, and hence signature, are influenced by nutritional status. The present invention may also be used to define adequacy of regional anesthesia or evaluation of pain response and the response to drug therapy with or without an automatic feedback component. It may also be used to identify and evaluate the presence of a drug substance and evaluate the initial response and/or therapeutic efficacy of a variety of pharmaceuticals. It can be used to track die agents and quantify their presence in association with blood flow parameters.

Other embodiments and uses of the invention will be apparent to those skilled in the art from consideration of the specification and practice of the invention disclosed herein. All references cited herein, including all international, United States and foreign patents and patent applications, for what ever reason, are specifically and entirely incorporated by reference including U.S. Pat. Nos. 5,441,053, 5,553,614, 5,377,003 and 5,528,368, and U.S. patent application Ser. Nos. 09/182,898, 09/389,342 and 60/165,970, and International Application Nos. PCT/US98/22961 and PCT/US99/20321. The specification and examples should be considered exemplary only within the true scope and spirit of the invention.

What is claimed is:

1. A method for evaluating a biological system or stimulus comprising the steps of:
   integrating spatial, spectral and temporal features, and optionally physiologic data, with a spectral and temporal multimodal imaging system;
   fusing a thermal image or other imaging modalities with said multimodal imaging system;
   registering multiple images acquired at various wavelengths and at different times in a hyperspectral cube so that each corresponding pixel in every plane images the same point in space; and
   incorporating a high spatial and temporal resolution imaging device as a reference in which each spectral image in the cube is registered to evaluate said biological system or stimulus.

2. The method of claim 1 further comprising the step of interlacing thermal images and hyperspectral images with a time-dependent reference.

3. The method of claim 1 further comprising the step of selecting a wavelength to maximize diagnostic information for a specific tissue state or anticipated end diagnostic goal.

4. The method of claim 3 wherein the selection step is performed by multivariate image and spectral processing algorithms to extract information from the plurality of images and spectra for real-time or near real-time assessment.

5. The method of claim 1 wherein the biological system being evaluated is skin.

6. The method of claim 1 wherein the biological system being evaluated is an organ or a tissue.

7. The method of claim 1 further comprising an analysis step to determine the spatial distribution of oxyhemoglobin, deoxyhemoglobin and methemoglobin.

8. The method of claim 7 wherein the analysis step further determines a total hematocrit by calculating the area under the oxyhemoglobin, deoxyhemoglobin and methemoglobin spectrum or the intensity at their respective wavelengths, and a total blood volume by pairing a total hematocrit with perfusion data from a broadband thermal camera.

9. The method of claim 7 wherein the analysis step further determines a state of perfusion, demonstrates state of oxygen extraction, or a state of neurohumoral, physiological or pathological circumstances in spatial patterns.

10. The method of claim 1 further comprising the step of gating each image of a hyperspectral image set as well as the thermal image or other imaging modalities to a biological function, to allow data collection from moving samples.

11. The method of claim 1 further comprising an analysis step that identifies and classifies chemical species other than hemoglobins.

12. The method of claim 1, further comprising the step of utilizing automatic feature extraction techniques to localize landmarks throughout the hyperspectral imaging cube.

13. The method of claim 1, further comprising the step of registering and analyzing multiple hyperspectral image sets taken over time.

14. The method of claim 1, further comprising the step of registering a hyperspectral image set with a three dimensional spatial medical image.

15. The method of claim 14 wherein the fusion is performed with a real-time or near real-time hyperspectral imaging device and a 3D medical image.

16. The method of claim 14 wherein the three dimensional spatial medical image is selected from the group consisting of MR, CT, PET, SPECT, ultrasound, or combinations thereof.

17. The method of claim 1, further comprising the step of performing real-time or near real-time visualization of the full spectral information at a given location by registering a real-time or near real-time trackable instrument with the images.

18. The method of claim 10 wherein the biological function is selected from the group consisting of a cardiac cycle, breathing, a pulse, and a muscle contraction.

* * * * *